(12) United States Patent
Boulanger et al.

(10) Patent No.: US 7,083,569 B2
(45) Date of Patent: Aug. 1, 2006

(54) OSTOMY CARTRIDGE

(75) Inventors: Jason Boulanger, New Baden, IL (US); Peter M. von Dyck, Fernandina Beach, FL (US); Steven White, Wellington, FL (US)

(73) Assignee: Zassi Medical Evolutions, Inc., Fernandina Beach, FL (US)

( * ) Notice: Subject to any disclaimer, the term of this patent is extended or adjusted under 35 U.S.C. 154(b) by 541 days.

(21) Appl. No.: 10/210,261

(22) Filed: Aug. 1, 2002

(65) Prior Publication Data

US 2003/0040727 A1 Feb. 27, 2003

Related U.S. Application Data

(60) Provisional application No. 60/309,961, filed on Aug. 3, 2001.

(51) Int. Cl.
*A61F 2/02* (2006.01)
*A61F 5/44* (2006.01)
*A61M 1/00* (2006.01)

(52) U.S. Cl. .................... 600/32; 604/277; 604/332
(58) Field of Classification Search ............ 604/327, 604/332–345, 277; 600/32
See application file for complete search history.

(56) References Cited

U.S. PATENT DOCUMENTS

| 3,528,419 A | 9/1970 | Joechle |
| 3,559,646 A | 2/1971 | Mullan |
| 3,595,233 A | 7/1971 | Fuchslocher |
| 3,867,924 A | 2/1975 | Bucalo |
| 3,996,933 A | 12/1976 | Gutnick |
| 4,232,673 A | 11/1980 | Bucalo |
| 4,266,022 A | 5/1981 | Lamprecht |
| 4,286,596 A | 9/1981 | Rubinstein |
| 4,308,867 A | 1/1982 | Roseman et al. |
| 4,318,405 A | 3/1982 | Sneider |
| 4,340,055 A | 7/1982 | Sneider |
| 4,381,765 A * | 5/1983 | Burton .................. 600/32 |
| 4,612,008 A | 9/1986 | Wong et al. |
| 4,668,227 A * | 5/1987 | Kay .................... 604/289 |
| 4,721,508 A * | 1/1988 | Burton ................ 604/338 |
| 4,878,905 A | 11/1989 | Blass |
| 4,941,869 A * | 7/1990 | D'Amico .............. 600/32 |
| 5,002,540 A | 3/1991 | Brodman et al. |
| 5,045,052 A | 9/1991 | Sans |
| 5,125,916 A * | 6/1992 | Panebianco et al. ...... 604/332 |
| 5,299,581 A | 4/1994 | Donnell et al. |
| 5,503,625 A | 4/1996 | Plass |
| 5,683,372 A * | 11/1997 | Colacello et al. ........ 604/333 |
| 5,769,813 A | 6/1998 | Peiler et al. |
| 5,840,055 A | 11/1998 | Sgro |
| 5,860,959 A | 1/1999 | Gent |
| 5,904,671 A | 5/1999 | Navot et al. |
| 6,007,525 A * | 12/1999 | Martell ................ 604/333 |
| 6,033,390 A * | 3/2000 | von Dyck .............. 604/332 |
| 6,096,057 A * | 8/2000 | Klingenstein ........... 606/197 |
| 6,485,476 B1 * | 11/2002 | von Dyck et al. ....... 604/332 |
| 6,595,971 B1 * | 7/2003 | von Dyck et al. ....... 604/334 |
| 2002/0091365 A1 * | 7/2002 | McNally et al. ........ 604/332 |

FOREIGN PATENT DOCUMENTS

WO     WO 90/07311     *  7/1990

* cited by examiner

*Primary Examiner*—Larry I. Schwartz
*Assistant Examiner*—M G. Bogart
(74) *Attorney, Agent, or Firm*—Husch & Eppenberger LLC; Rebecca J. Brandau

(57) ABSTRACT

An ostomy cartridge for use in host device in a mammal includes a body formed at elastomeric partially of polymeric material and a stem. The stem is secured to the body and is operable to permit insertion of the body into the host device and removal of the body from the host device. The stem and the body cooperate with one another and the host device to prevent flow of liquid and solid waste through the host device to the exterior of the mammal with which the host device is associated.

45 Claims, 20 Drawing Sheets

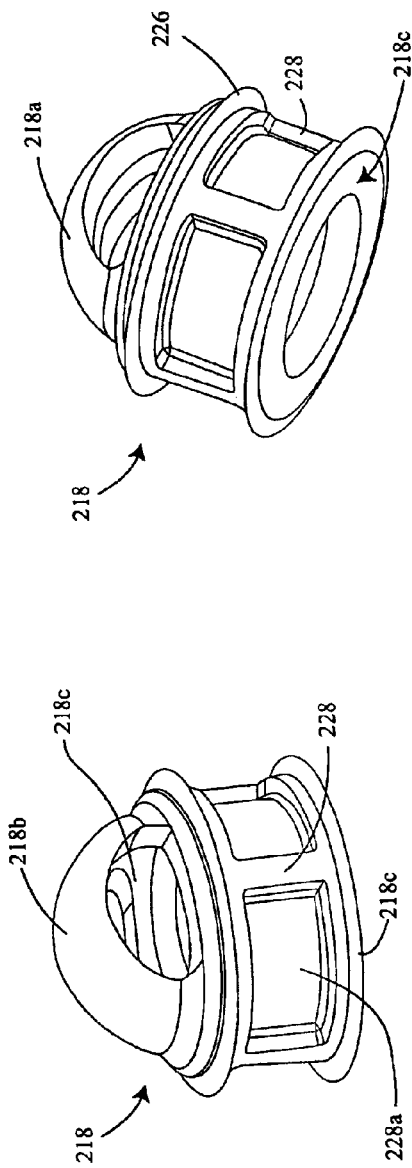
Figure 28
Figure 29
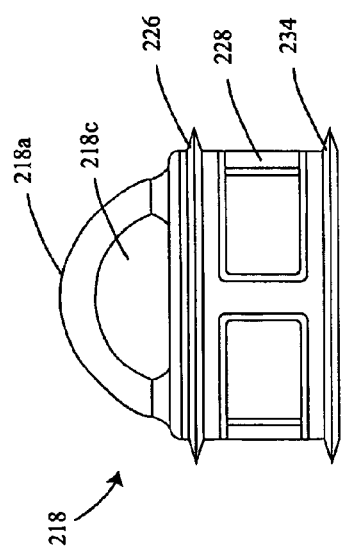
Figure 30

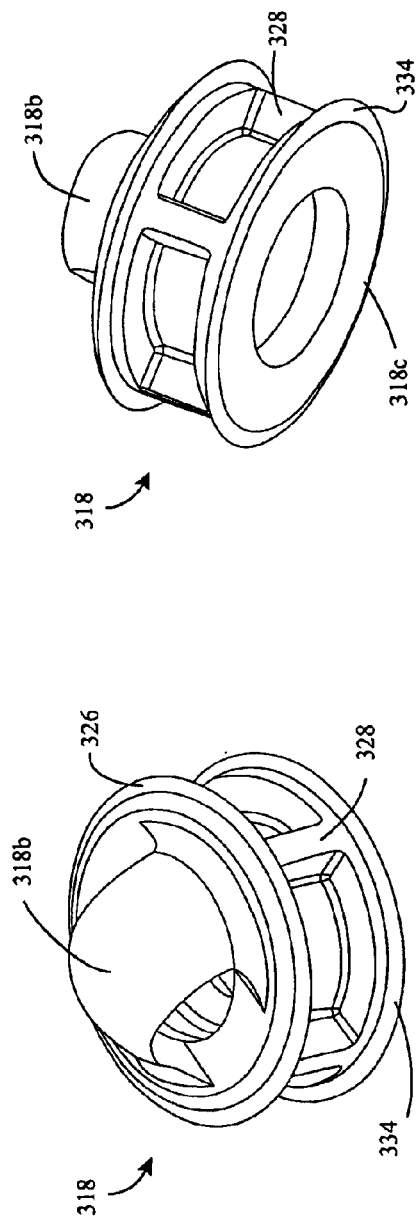
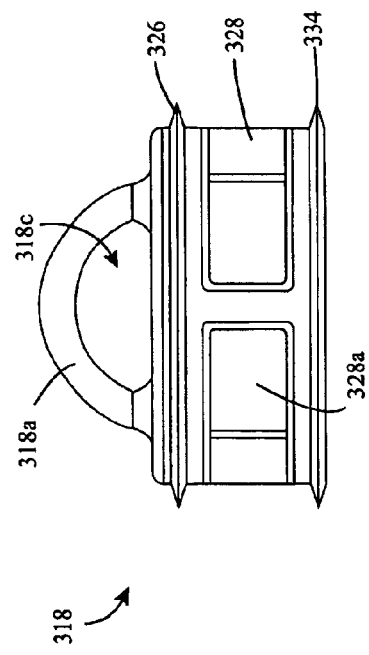
Figure 37
Figure 38
Figure 36

OSTOMY CARTRIDGE

CROSS-REFERENCE TO RELATED APPLICATIONS

This application claims the benefit of the filing date of Provisional Application 60/309,961, filed Aug. 3, 2001.

This case claims the benefit under 35 U.S.C. 119(e) of U.S. Provisional Patent Application No. 60/354,532 filed Feb. 5, 2002.

FIELD OF THE INVENTION

The present invention relates generally to the field of ostomy accessories, and, more specifically, to a cartridge for use, for example, in an ostomy port or other host device, to prevent escape of bodily wastes while simultaneously permitting the release of intestinal gases.

BACKGROUND OF INVENTION

Previously, devices were marketed in attempts to provide continence through stomal occlusion by foam plugs having a coating. However, the foam structure in combination with the coating did not provide sufficient permeability to gases for relief while in situ. Other devices used charcoal and other odor absorbing technologies to capture waste and emitted flatus, such as in bag appliance. However, these odor "scrubbing" agents have had the disadvantage of not being protected by an effective occluding barrier to moisture. Thus, the odor scrubbing media have often failed due to unavoidable body fluid contact with the media.

Tampons, such as those marketed under the registered trademark TAMPAX, and other tampon-like products have been produced from fiber materials with the intent of occluding body fluids for other purposes. None of these materials have been transferred to the application of occluding the gastrointestinal tract through stomas or secondary access systems, such as catheters, stents or ports. A plug device, marketed under the trade name "Conseal" is the only known products that has been used in an attempt to occlude access to the GI tract through a stoma, while self-expanding an anchoring foam bolster that encountered both gases and liquid/solid matter. The Conseal plug essentially occluded all substances through the plug, including gases, and thus is unsatisfactory for the present usage contemplated.

The known art, where applied to GI tract access has provided occlusion of contents, including gas, so as to not allow soiling at the skin level access to the device. The attempts to use open-cell foams of high hydrophilicity for swelling and creating a sealing mechanism are largely ineffective at allowing sustained gas release through the foam of the device. Other known devices offer complete occlusion of GI tract contents without discriminating between the release of produced gases and solid or liquid waste.

SUMMARY OF INVENTION

While, for the most part, the discussion herein involves the use of the described cartridge with ostomy ports, for simplicity of discussion, it is to be understood that the new device is intended to also be capable of adaptation for use as a flatus deodorizing cartridge or system for relief and odor scrubbing of through ports, stents or catheters (host devices) which provide access to the host's gastrointestinal system from the exterior of the mammal. Thus, when the term "port" is used, it is intended to encompass all such host devices. In order to provide clear examples of the types of ostomy ports with which the new cartridge is considered to be useful with the invention, the reader is referred to U.S. Pat. No. 6,033,390, issued Mar. 7, 2000, and pending application U.S. Ser. No. 09/477,204, filed Jan. 4, 2000, the disclosures of such documents which are incorporated herein by reference, in their entireties.

Regardless of the type of port, stent, catheter, etc., with which the invention is used, it is an advantage of the present invention that the new cartridge is constructed in a manner which permits simultaneous release of gases, yet retains/blocks all passage of liquid and solid matter by occlusion (interference fit) within the host device, along with absorption properties. It is further among the objects of the present invention, having the features listed, that the new cartridge allow for gas to channel, permeate and otherwise migrate through the cartridge structure, or between the structure and the host device lumen for effective release. The new cartridge device is desired to be disposable on a routine basis for purposes of maintaining gas flow patency properties, functional deodorization and sanitation of the host device, and it provides a wiping function of the host device pathway or lumen during insertion.

Accordingly, in keeping with the above objects and advantages, the present invention is, briefly, an ostomy cartridge for use in a mammal, the cartridge permitting passage of gas while simultaneously preventing discharge of solid and liquid waste through the ostomy. The invention is further, briefly, a cartridge device composed generally of a stem portion and a body portion mounted to the stem portion, wherein the body portion is sized and shaped appropriately to fit slidingly and snugly within an ostomy port or other host device and the body portion is formed of material which permits passage therethrough of bodily gases and which discourages escape through the host device of liquid and solid waste matter.

These and other advantages and goals of the invention will be in part apparent and in part pointed out hereinbelow.

BRIEF DESCRIPTION OF THE DRAWINGS

FIG. 28 is a reduced proximal perspective view of the plunger of FIG. 23.

FIG. 29 is a reduced distal perspective view of the plunger of FIG. 23.

FIG. 30 is a reduced side elevational view of the plunger of FIG. 23, taken at a 90 degree rotation of FIG. 25.

FIG. 36 is a reduced proximal perspective view of the plunger of FIG. 31.

FIG. 37 is a reduced distal perspective view of the plunger of FIG. 31.

FIG. 38 is a reduced side elevational view of the plunger of FIG. 31, taken at a 90 degree rotation of FIG. 33.

Throughout the drawings like parts are indicated by like element numbers.

DESCRIPTION OF PRACTICAL EMBODIMENTS

Figure 1:
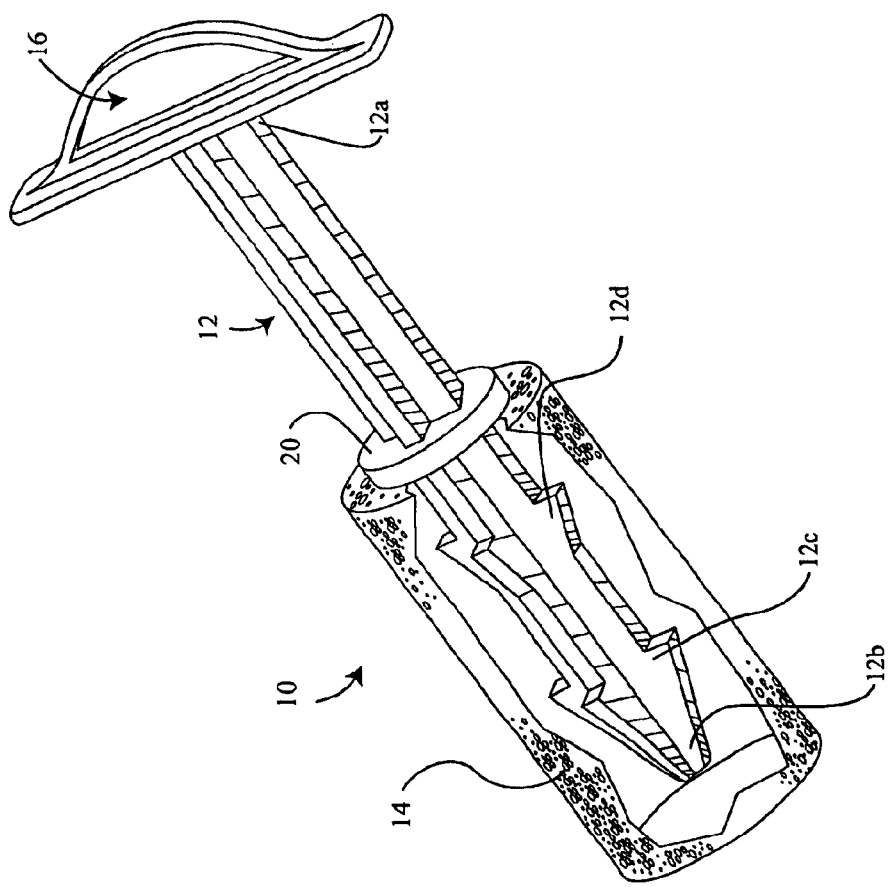
FIG. 1 is an enlarged perspective, schematic view of an ostomy cartridge constructed in accordance with and embodying the present invention.

With reference to the drawings, and specifically FIGS. 1–10, there is illustrated a cartridge, generally designated 10, constructed in accordance with and embodying the present invention. Cartridge 10 is composed of a stem portion, generally designated 12 and a substantially cylindrical body portion 14. The stem 12 has spaces 13 that provide gas flow channels. Stem 12 is preferably formed of polypropylene, although other medically suitable materials can be used. In one embodiment, the stem 12 provides localized structural support for the host device (not shown). The spaces 13 of the stem 12 also provide for relative movement of the host device. Body portion 14 is preferably formed of a foam material, as will be discussed further hereafter. Throughout the Figures, dimensions shown on the drawings are to be understood to be in inches and are provided to illustrate representative examples of dimensions.

Figure 9:
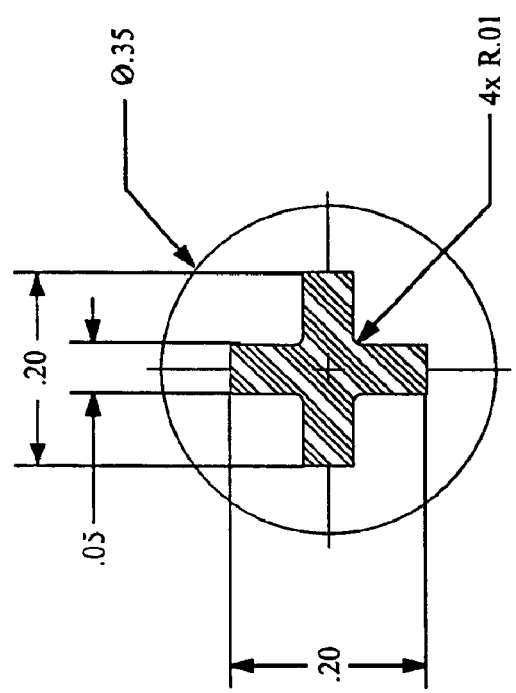
FIG. 9 is an enlarged sectional view taken on line E—E of FIG. 6.

In the preferred embodiment, stem 12 is elongated and has a "cross" shape in transverse section, as illustrated in FIG. 9. However, other transverse-sectional shapes are conceived that will suffice. Stem 12 may be rigid or flexible allowing for conformity to the host device and to a patient's stoma track (not shown). Stem 12 is optionally provided with a handle 16 on one end 12a, which stem end 12a is disposed distally with reference to the patient's body during normal use of cartridge 12. Handle 16 can be fixed to stem end 12a, or selectively removable therefrom and preferably has a low profile and no sharp corners or edges, so as not to snag the user patient's skin or clothing. Further, handle 16 may be substantially solid in structure, or may have an open central area surrounded by a flexible gripping area, as shown, The shape of handle 16 as illustrated in FIG. 1 is merely one example of a useful appropriate construction therefor and other useful shapes will be apparent to one skilled in the art.

Figure 3:
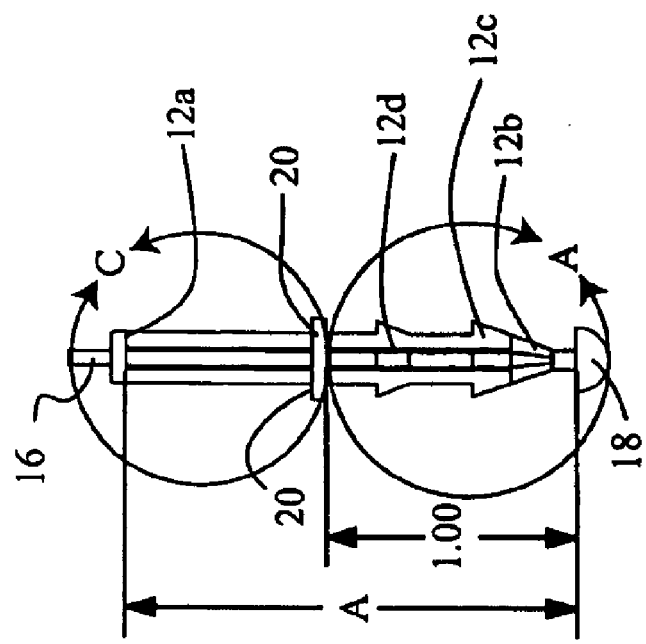
FIG. 3 is a side elevational view of the stem portion thereof.
Figure 2:
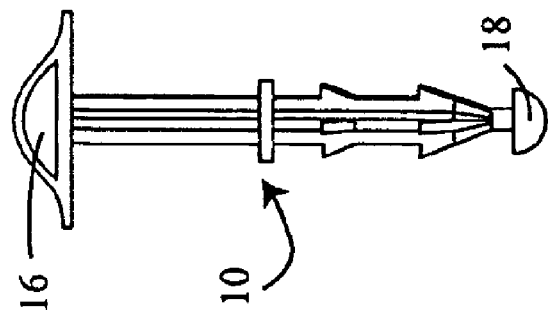
FIG. 2 is a side elevational view of the stem portion thereof, without the body portion.
Figure 5:
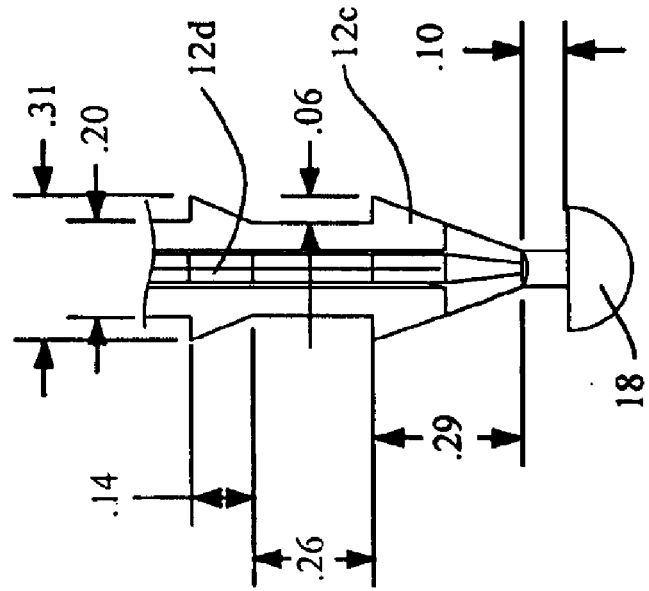
FIG. 5 is an enlarged side elevational view of the lower portion of FIG. 3.
Figure 4:
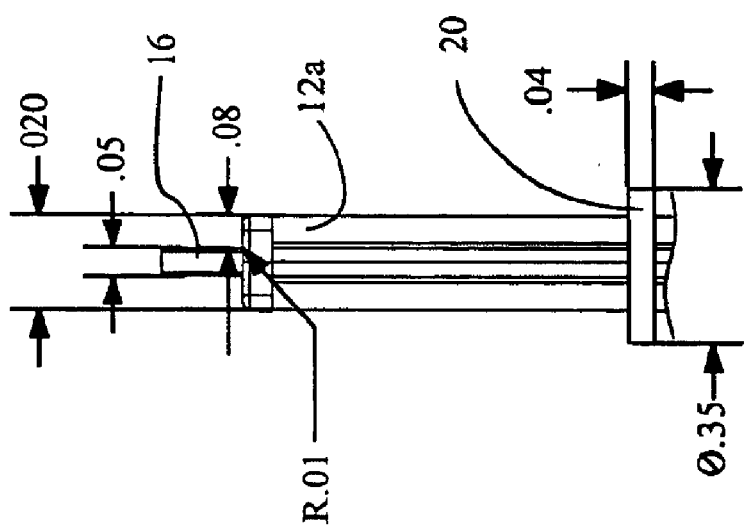
FIG. 4 is an enlarged side elevational view of the upper portion of FIG. 3.
Figure 6:
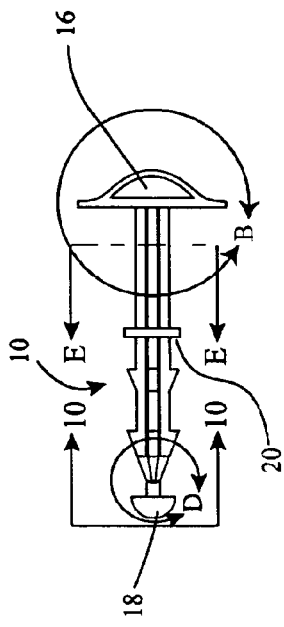
FIG. 6 is a side elevational view of the device of FIG. 2, shown horizontally and indicating where enlarged figures and sections are taken.
Figure 8:
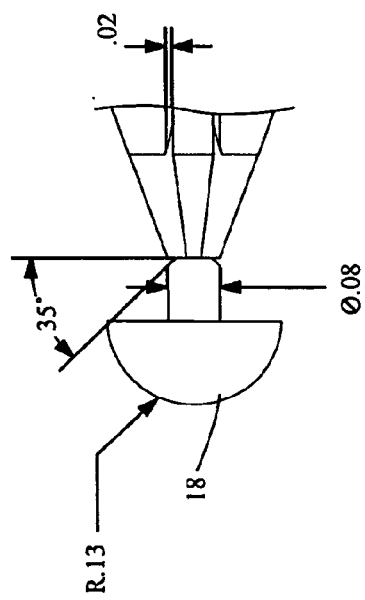
FIG. 8 is an enlarged side view of the tip portion of FIG. 6.
Figure 7:
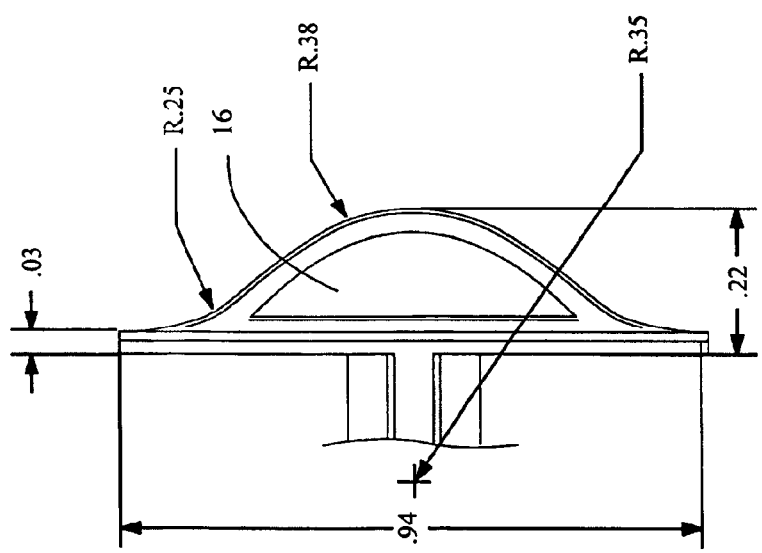
FIG. 7 is an enlarged side view of the handle portion of FIG. 6.
Figure 10:
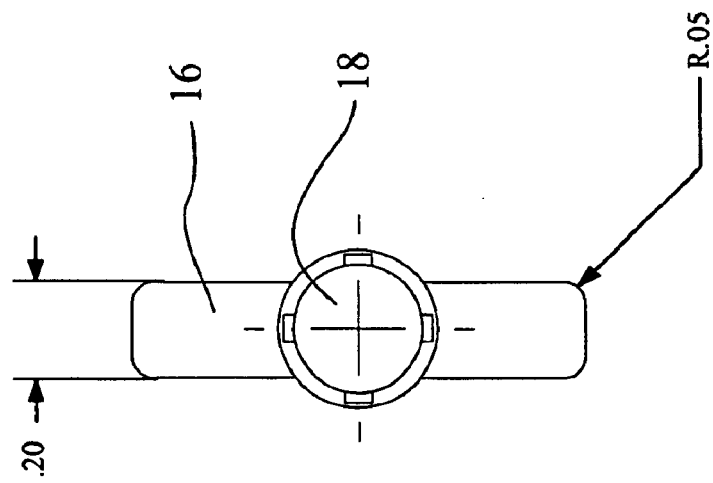
FIG. 10 is an end elevational view taken from the direction of line 10—10 of FIG. 6.

The opposite end 12b (proximal with reference to the patient's body) of stem 12 is molded or otherwise shaped into a nose cone (such as illustrated in FIG. 1, or a more elaborate dome-shaped flange 18, as illustrated in FIGS. 2, 3, and 8, for example. Other stem end 12b shapes are conceived that will certainly suffice. Tip 18 on stem end 12b is surrounded by body 14 in the completed cartridge 10, so that tip 18 is not exposed, in order to protect the patient from any possibility of trauma from tissue contact with tip 18.

Around at least a portion of stem 12, relatively nearer to proximal end 12b than to distal end 12a, stem 12 has molded or shaped radially and spaced-apart protruding members, such as those indicated at 12c, 12d, for example. Protruding members 12c, 12d serve to anchor or otherwise secure body 14 to stem 12, so that cartridge 10 can be introduced and removed as a unit, into and out of the host device (not shown), without separation of body 14 from stem 12.

FIGS. 1, 2–4, 6 and 9 illustrate a transverse, radially extending flange ring 20 disposed substantially midway along the length of stem 12. Ring 20 serves as a distal end point for body 14 on stem 12.

Body 14 is preferably formed of a foam material, which can be molded directly to stem 12, between protruding elements 12c, 12d (for example) and around stem end 12b, regardless of the presence or absence of a tip, such as 18. The foam, if molded foam has a relatively greater degree of closed cell structure. Alternatively the foam can be cast as a sheet and die cut to the desired shape, as shown. Cast foam of this type will have a greater relative degree of open cell structure, as compared to molded foam. Because of the skin on the cartridge the foam can have both open and closed portions and thus gas can pass through the foam portion of the body. If die cut, the foam of body 14 can be cut longitudinally with a cruciate, cross, slit, or other pattern, through which a stem 12 can be inserted to the appropriate depth for anchoring. Foam body 14 is secured to stem 12 by mechanically locking of the selected stem 12 detail into the foam.

As an alternative to molding, foam body 14 can be fixed to stem 12 for mechanical integrity and anchoring, by mechanical methods, as described, or optionally can be glued or otherwise connected to stem 12. Alternative shapes to foam body 14 can be cylindrical, partially spherical, i.e., segments of sphere, ribbed, or other contours to permit effective interference fit to the host device lumen wall. For example successive partially spherical segments allow gases to flow through wall interference and interstitial pores of foam to release into less restrictive expansion zones in between spherical segments.

Another alternative design allows for alternative ribs of foam compressed at the wall of the host device lumen with air gaps between ribs for gas back pressure reduction as gas progresses beyond each rib. Permeable foam (open cell) allows for gas passage and diffusion. In any case, ribs may be formed by molding or by banding foam with tape or other material to create narrowed diameters between fully expanded foam ribs with unrestricted diameters. Any of the above-mentioned foam shapes can be laminated (not shown) at the proximal tip 12b, with a hydrophobic scrim, non-woven, or polymeric membrane to create a barrier to solids and liquids permeation to foam member behind laminated layer. Such barriers can be usefully positioned distal to termination of the lumen in the host device, for example. Further, the foam used can be selected to be of a type that will allow wicking and collection of liquids, yet provide gas permeation pathways in cellular interstices.

As a further alternative to the described embodiment, foam body 14 can be wrapped or otherwise enclosed in a hydrophobic membrane formed of a non-woven material, or in a high moisture vapor transmission membrane (not shown), as however may be preferred to create a barrier to solids and liquid permeation of foam body 14.

FIGS. 11–22 illustrate another embodiment of a cartridge, generally designated 110, constructed in accordance with and embodying the present invention. Cartridge 110 is composed generally of an elongated stem 112, having an optional handle 116 at a first stem end 112a, and a proximal tip 118 and fecal guard 120 mounted at a second, opposite stem end 112b. As in the first discussed embodiment, stem 112 has a transverse sectional configuration, which is preferably, although not necessarily, cross-shaped, but in this embodiment this structure extends along substantially the entire length of the stem. The elongated spaces 113 remaining between adjacent arms 112c of the cross provide longitudinal channels for flow-through of gases, just as is the case with the first-described embodiment. An annular flange 122 is disposed at end stem 112b, in order to assist in connection of tip 118 and fecal guard 120 to stem 112.

Figure 11:
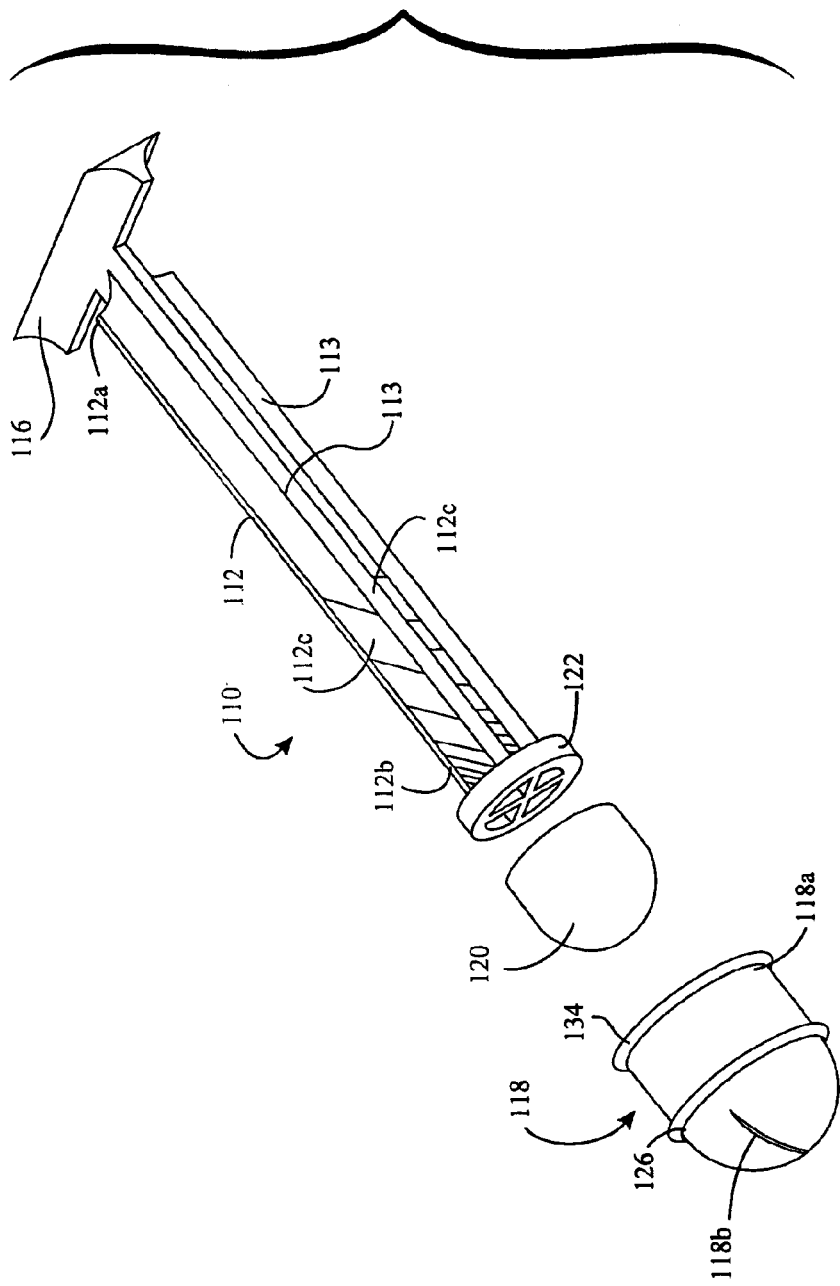
FIG. 11 is an enlarged exploded view of another embodiment of a cartridge constructed in accordance with and embodying the present invention.
Figure 13:
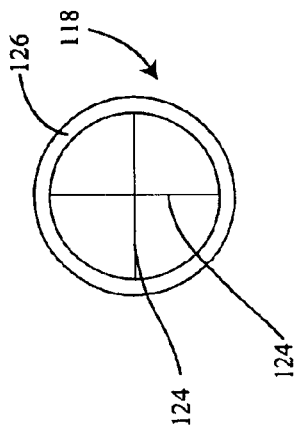
FIG. 13 is plan view of the tip shown in FIG. 12 taken from the top of the figure.
Figure 15:
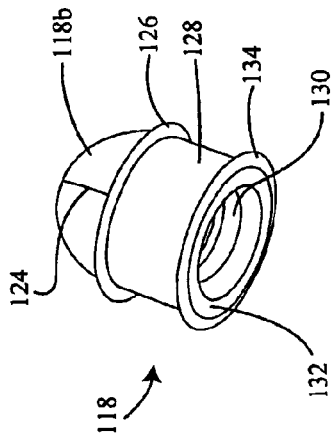
FIG. 15 is a perspective view of the tip shown in FIG. 12.
Figure 12:
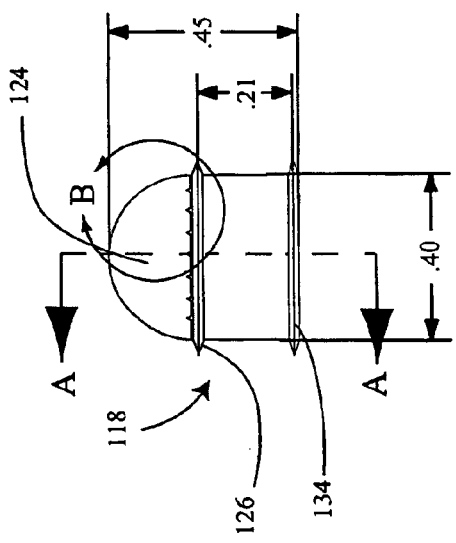
FIG. 12 is a side elevational, schematic view of a tip portion of the embodiment of FIG. 11.
Figure 14:
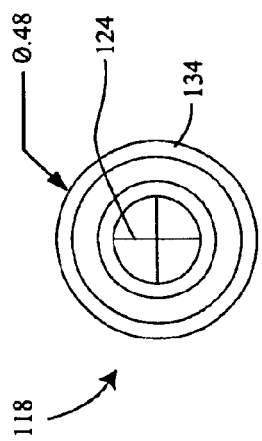
FIG. 14 is a bottom (distal) plan view of the tip shown in FIG. 12.
Figure 17:
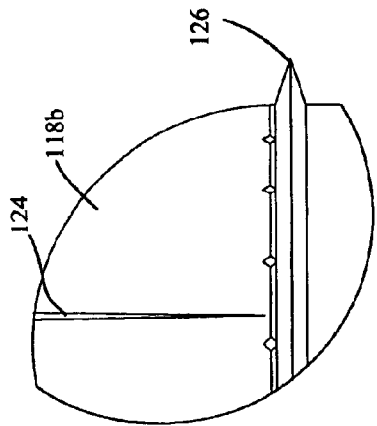
FIG. 17 is an enlarged partial view of the tip shown in FIG. 12.
Figure 16:
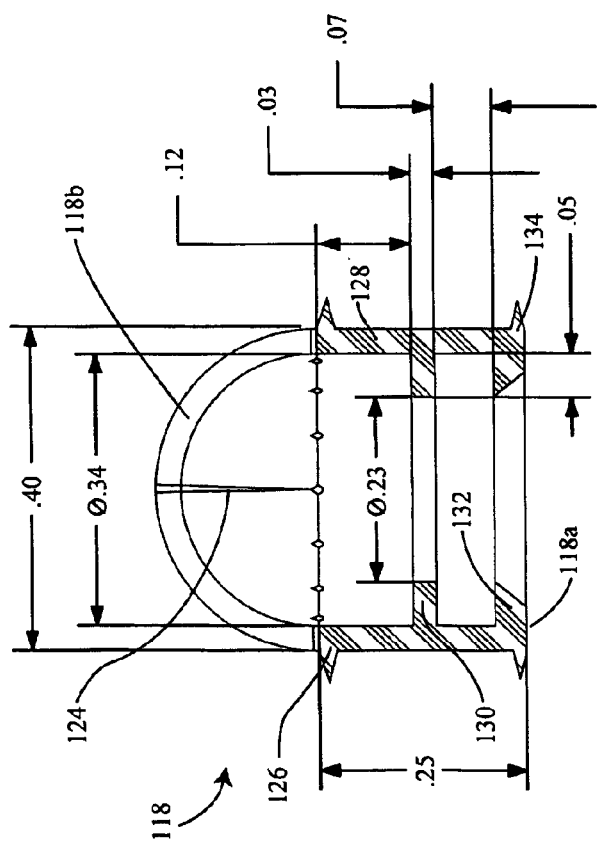
FIG. 16 is an enlarged sectional view taken on line A—A of FIG. 12.
Figure 19:
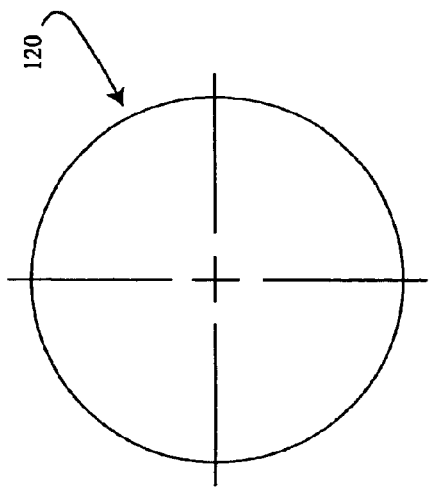
FIG. 19 is a plan view taken from the top of FIG. 18.
Figure 20:
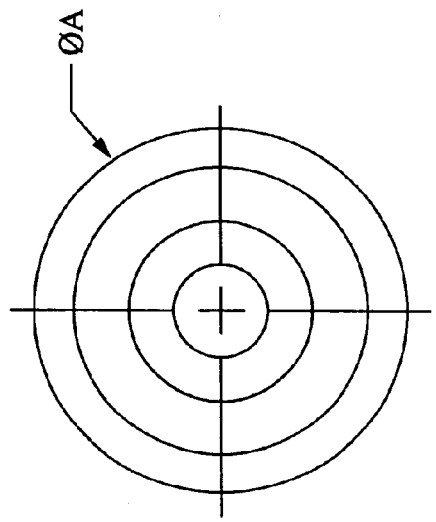
FIG. 20 is a plan view taken from the bottom of FIG. 18.
Figure 18:
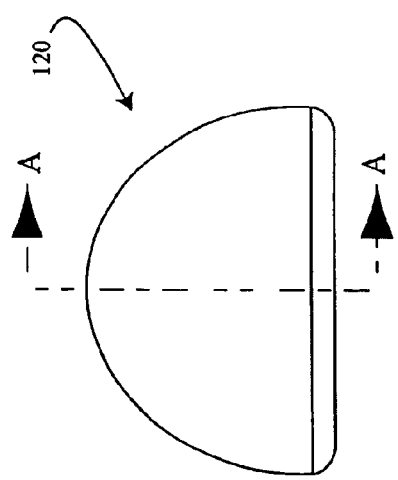
FIG. 18 is a side elevational view of the fecal guard portion of the embodiment shown in FIG. 11.
Figure 22:
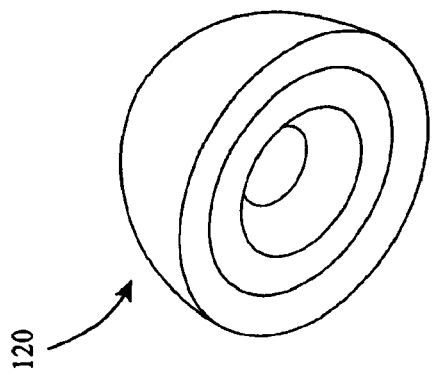
FIG. 22 is a perspective view of the fecal guard of the cartridge embodiment shown in FIG. 11.
Figure 21:
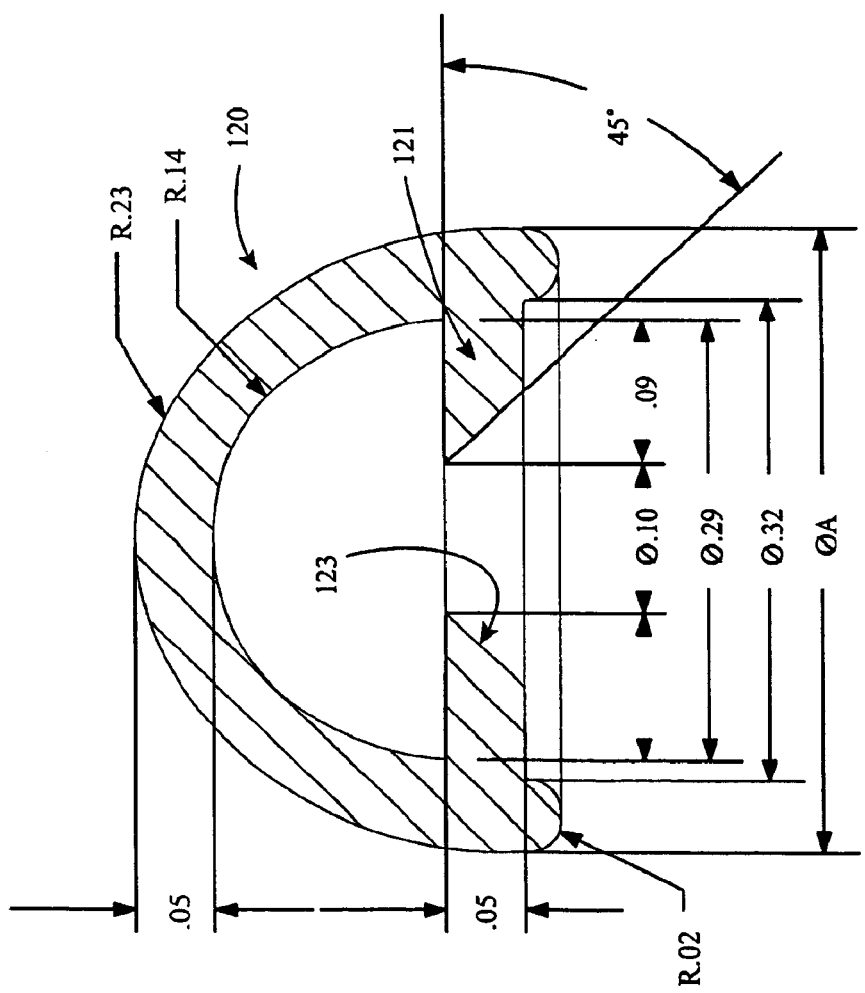
FIG. 21 is a sectional view taken on line A—A of FIG. 18.
Figure 23:
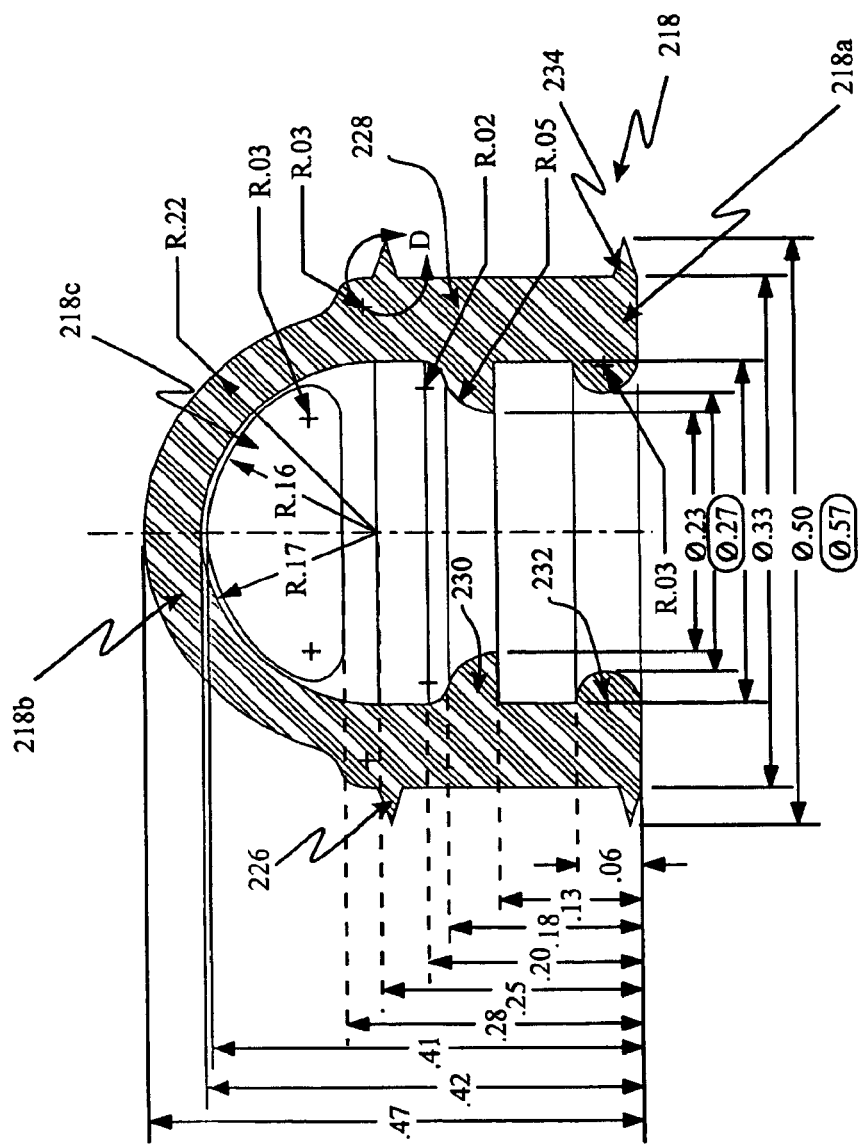
FIG. 23 is a longitudinal sectional view of another embodiment of the plunger (tip) portion of the cartridge of FIG. 11, taken on line A—A of FIG. 25.
Figure 25:
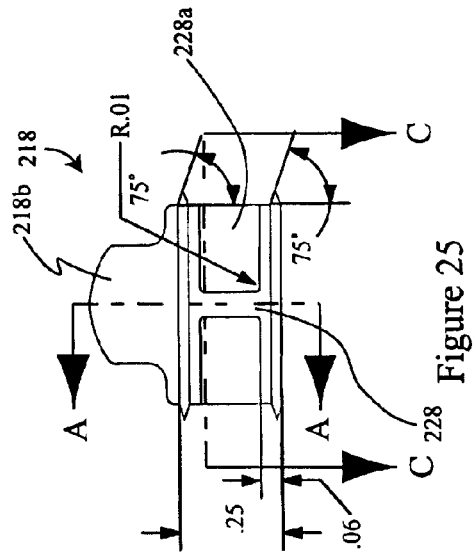
FIG. 25 is a schematic side elevational view of the plunger shown in FIG. 24.
Figure 27:
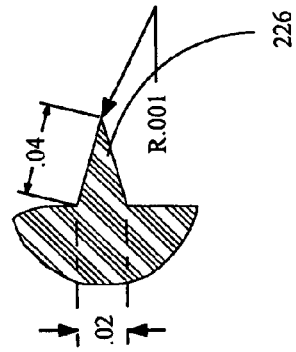
FIG. 27 is an enlarged partial sectional view taken from FIG. 23.
Figure 24:
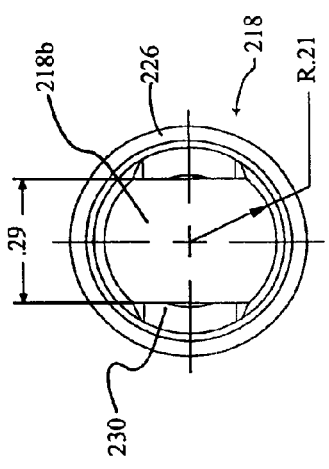
FIG. 24 is a schematic top plan view of the plunger shown in FIG. 23, reduced.
Figure 26:
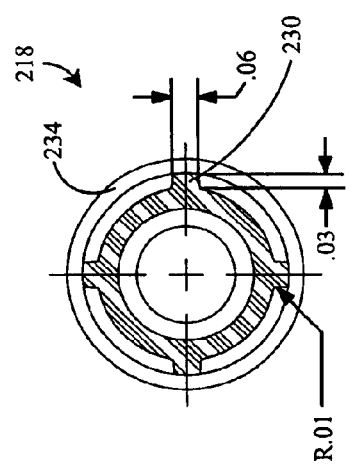
FIG. 26 is a transverse sectional view taken on line C—C of FIG. 25.
Figure 31:
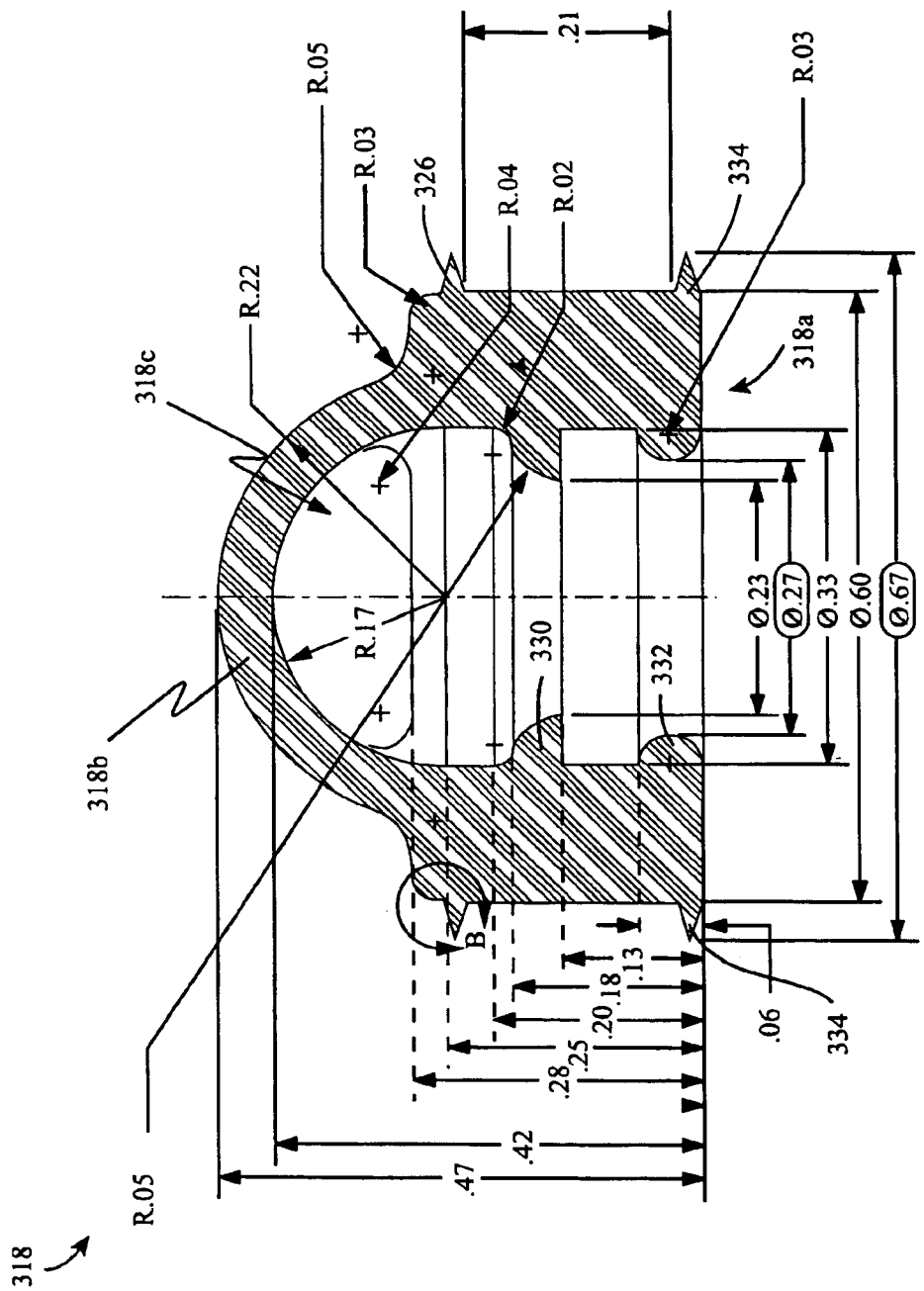
FIG. 31 is a longitudinal sectional view of still another embodiment of the plunger (tip) portion of the cartridge of FIG. 11, taken on line A—A of FIG. 33.
Figure 33:
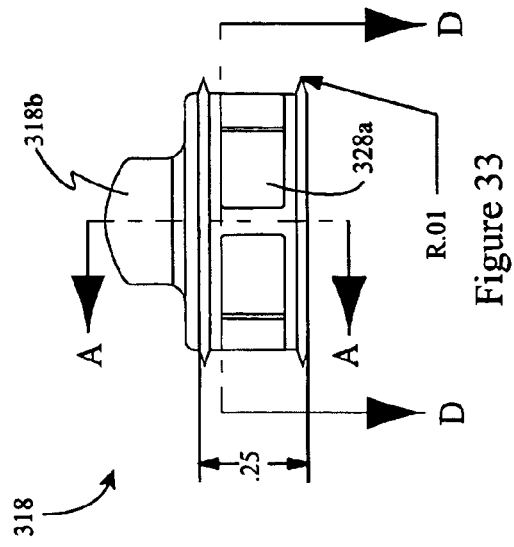
FIG. 33 is a schematic side elevational view of the plunger shown in FIG. 32.
Figure 35:
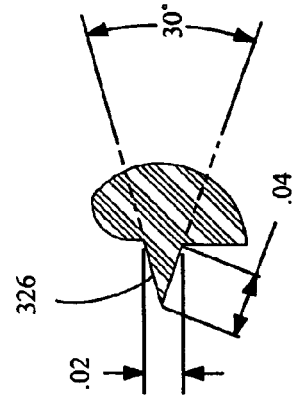
FIG. 35 is an enlarged partial sectional view taken from FIG. 31.
Figure 32:
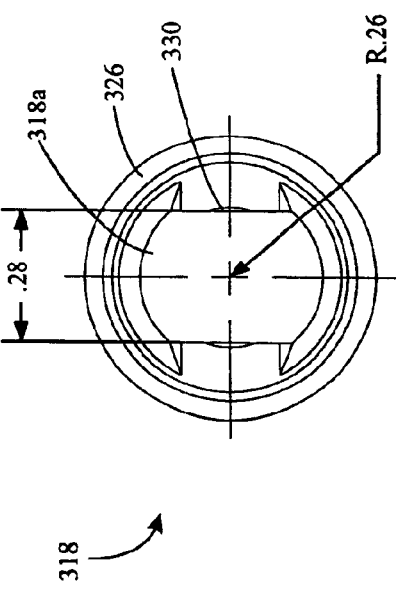
FIG. 32 is a schematic top plan view of the plunger shown in FIG. 31, reduced.
Figure 34:
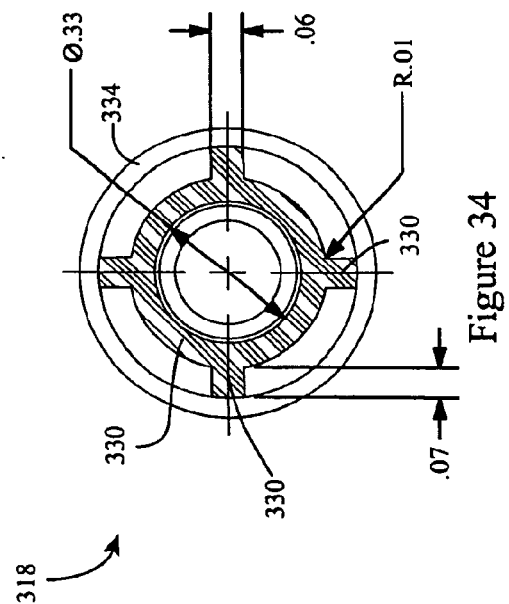
FIG. 34 is a transverse sectional view taken on line D—D of FIG. 33.
Figure 39:
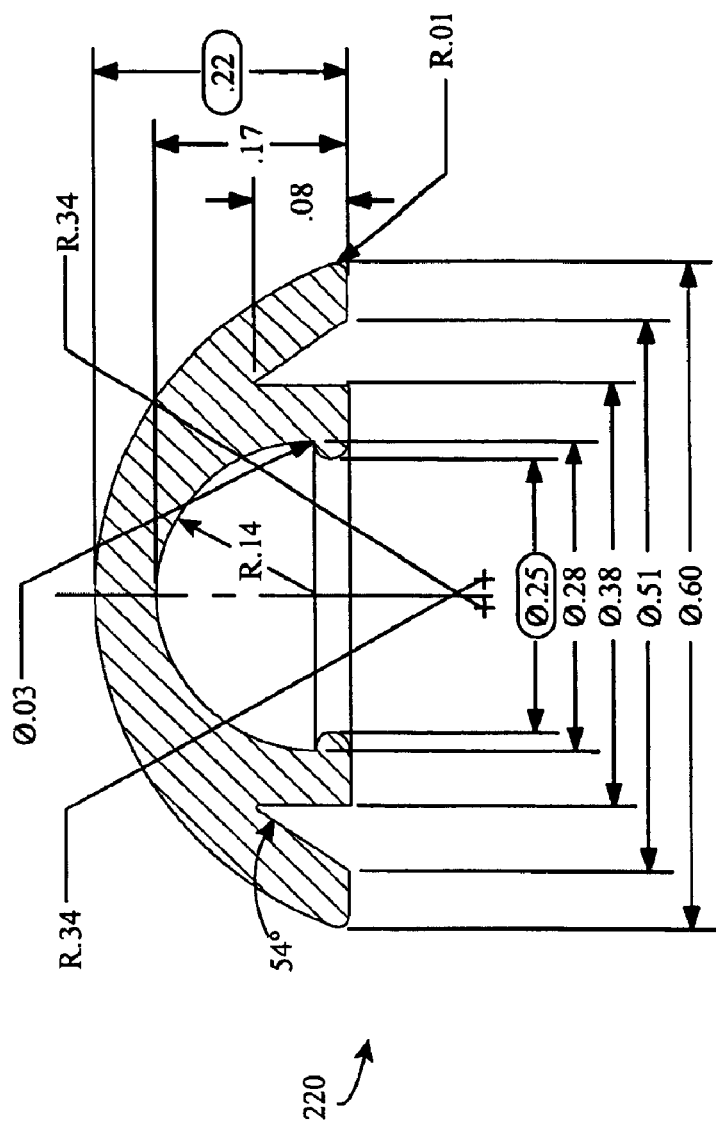
FIG. 39 is a longitudinal sectional view of an alternative embodiment of the fecal guard portion of the cartridge shown in FIG. 11.
Figure 40:
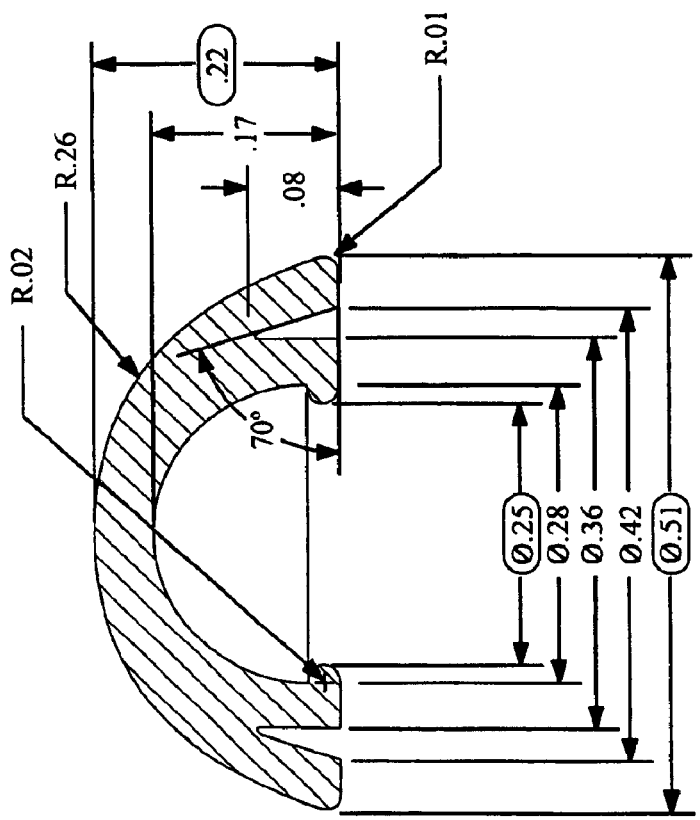
FIG. 40 is a longitudinal sectional view of a still further embodiment of the guard portion of the cartridge of FIG. 11.
Figure 41:
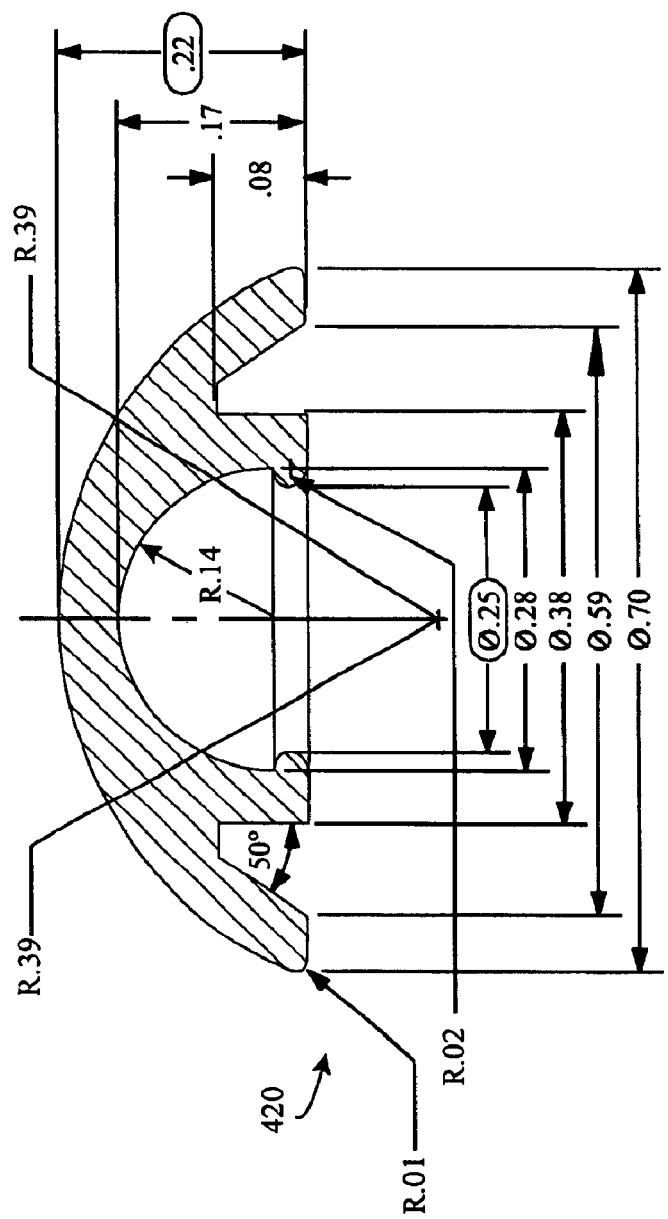
FIG. 41 is a longitudinal sectional view of another embodiment of the guard portion of the cartridge shown in FIG. 11.
Figure 42:
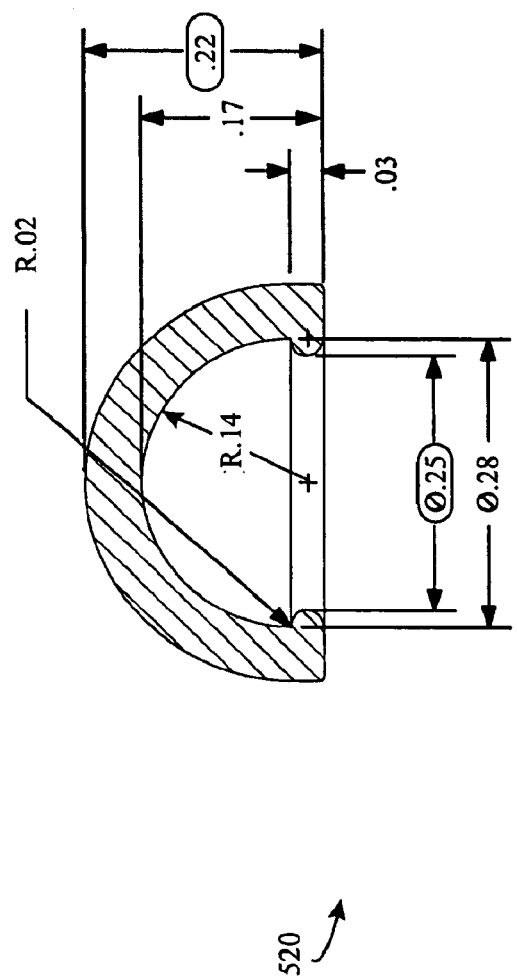
FIG. 42 is a longitudinal sectional view of still another embodiment of the guard portion of the cartridge shown in FIG. 11.

As in the first embodiment, handle 116 can take a variety of useful forms, but is shown in FIG. 11 as a straight member mounted transversely to stem end 112a. Handle 116 may be molded directly to stem 112, or mechanically bonded thereto by any known appropriate means.

FIGS. 12–17 schematically illustrate the detail the shape and dimensions of the preferred construction of tip 118 which is insertable and retractable from the patient/host port, wiping the interior side wall of such host device as it is inserted and withdrawn. As seen in the Figures, tip 118 preferably has an annular open end 118a (distal end) and a generally dome-shaped patient proximal end 118b. Tip 118 is preferably molded of an elastomeric material, such as polyurethane, with holes or slits, such as indicated at 124, for example. Slits 124, or other variations thereof expose fecal guard 120, and subsequently pathways 113 for gas escapement while preventing solid materials from entering or fouling the pathways.

While variations on the construction of tip 118 can be conceived (and some of which are to be described later herein), in the embodiment shown in FIG. 11, the slitted, domed end 118b terminates distally in an annular ridge 126 which is formed at the proximal extreme of a cylindrical wall 128. Approximately midway along an interior surface of annular wall 128 is formed an internal annular shoulder 130 which serves to engage and seat annular flange 122 on stem 112 on a proximal side of flange 122. The distally directed side of flange 122 is retained in position within tip 118 by a further annular shoulder 132 formed internally of tip 118 at the distal end 118a thereof. End 118a also carries an annular flange 134 on the external surface thereof to provide wiping action as cartridge 110 is inserted and/or removed from the host port (not shown). Thus flange 122 is securely seated between the two internal shoulders, 130, 132, to prevent accidental disengagement of stem 112 from tip 118.

In the preferred form of cartridge embodiment 110, tip 118 is backed by a guard 120 which is preferably formed of foam (e.g. polyurethane) and dome-shaped. The structural details of the preferred guard 120 are shown in FIGS. 18–22, wherein dimensions are shown in inches. Due to reproduction anomalies, the Figures shown are not necessarily exactly to the scales specified. When formed as shown for use with cartridge 110, guard 120 is substantially hemispherical, with an internal annular flange 121. Flange 121 defines a throughhole 123 for receipt of annular flange 122 on stem end 112b. For ease of insertion and to discourage ready removal of stem 112 from guard 120, an internal edge of flange 121 tapers inwardly, toward the central axis of guard 120. The material of guard 120 is to be formed of a foam that will provide liquid absorption (and blocking of solids) while remaining permeable to gas migration behind the distal elastomeric tip member 118 with its pathways/slits 124 for gas flow.

FIGS. 23–30 illustrate in detail an alternative embodiment, generally designated 218, of the tip of the new cartridge that is usable, as is tip 118, with a guard 120. Dimensions shown in the Figures are a practical useful form of the tip 218, but it is to be kept in mind that, as with other Figures shown herein, due to reproduction anomalies, the drawings shown may not be completely accurate to the proportions indicated. Tip 218 is preferably formed of an elastomeric polymer, for example, a polyurethane material, such as that sold as "Pellethane 2103-70A" by the Dow Plastics company. While the overall size of tip 218 may vary, the distal circumference of tip 218 should be contiguous and completely formed for a proper seal within the host device, although a center area defined by the tip is open and accessible via spaced-apart openings 228a formed in the cylindrical side wall 228 which extends between proximal tip end 218b and distal tip end 218a. As in the embodiment previously described, tip 218 has an annular external flange 234 at the distal end thereof and an internal annular shoulder 232 at end 218a. Proximally and spacedly from shoulder 232 there is a second "shoulder" 230, which in this embodiment is not contiguous, but is broken or separated by the openings 228a formed in wall 228. Proximally of flange 234 and at the proximal extreme of wall 228 is another annular external flange 226, shown enlarged in FIG. 27, and for the same sealing/wiping purpose as in the embodiment shown in FIG. 16.

Proximally of flange 226 tip 218 forms an arcuate end 218b, which has spaced apart openings 218c for facile passage into the cartridge of gases. While two such openings 218c are illustrated, conceivably more or less than two such openings will also function adequately.

FIGS. 31–38 illustrate a further embodiment, generally designated 318 of the tip for use with the cartridge of FIG. 11. As the structure and function of tip 318 is very similar to tip 218, corresponding element numbers (except denoted by 300 series numbers instead of 200 series number) have been shown on corresponding elements and are to be understood to be structure and to function in similar manner. Further textual description is not provided, to avoid unnecessary repetitiveness in the specification hereof. Essentially, the differences between the two embodiments, 218 and 318 are merely of dimensions and it is to be understood that these are only two examples of acceptable forms of the proposed tip for cartridge 110.

FIGS. 39, 40, 41 and 42 illustrate alternative embodiments 220, 320, 420, 520 respectively, of the fecal guard used in association with cartridge 110. While each embodiment has a generally open domed shape, as does the first embodiment, 120, there are illustrated variations in the overall dimensions and curvatures. Embodiments 220, 320 and 420 each include an annular groove formed in the distal face of the guard. The grooves are illustrated to have varying angles and depths in the various embodiments. By contrast, guard 520, illustrated in FIG. 42 lacks an annular groove, but, like guards 220, 320 and 420, does carry an internal annular shoulder at the distal end of the guard. The dimensions of the internal shoulders vary for the different embodiments, as illustrated. The five embodiments of the cartridge fecal guard shown and described herein are to be considered to be only examples of suitable waste guards that will function acceptably as part of the cartridge of FIG. 11. In each case, the preferred material for forming the guard is the same polyurethane foam as described in the discussion of tips 218, 318, although other suitable materials can be substituted as long as they permit passage therethrough of gases and simultaneously provide blockage of body wastes.

Alternative forms (not shown) of the new cartridge are made of polyurethane foam sheet of about one eighth inch to about one quarter inch thickness, with a laminated layer of non-woven polyethylene or polypropylene scrim of about 0.010 inch to about 0.030 inch thickness adhered by adhesive to one side of the foam. The foam material can contain dispersed and retained odor scrubbing media such as activated charcoal. Composite materials can be attached to a stem support system, for example as follows:

a). by winding around a stem core so that multiple layers are produced in a cylinder cartridge, wherein the cartridge provides alternating layers of absorptive foam and high moisture-vapor permeable materials allowing bi-directional flow of gases through layers axially and radially;

b). by pleating the foam over a preselected distance from the tip and along the cylinder to provide preferential gas/liquid conduits without occlusion from solid waste materials;

c). by forming the cartridge of single layer laminated foam/non-woven substrate as described and then pleating and wrapping around the stem support to expose the pleats along the axial direction of the stem; and d). by wrapping a single layer of composite material as described above around a spindle with an internal air volume for channeling of gas that has permeated the wrapped layer.

It is also conceived that a cartridge can be formed as described above and have an odor scrubbing component of activated charcoal or other know active ingredient preferential to the adsorption of hydrogen sulfide and like gases know to be included in human flatus. Such odor scrubbing element can be included in a reticulated foam structure formed into a sheet about 0.020 inch to about 0.200 inch thick, and laminated to non-woven or polymeric membrane layer(s) with adhesive for effective moisture barrier, and cut or punched into a disk or other geometric shape, as may be useful and preferred. The odor scrubbing compounds may also be suspended in minerals or other filler materials to form a semi-porous bed of dry solid material to be loaded into a containment compartment. Such finished scrubbing element of either type described above can be fixed into a compartment or against a supporting flange making up the proximal segment of the cartridge stem.

The compartment or flange, as described directly above provides retention of odor scrubbing element and seals against the inner lumen wall of the host device so that gas is preferentially channeled through the odor-scrubbing element. In use of the proposed device, gas passes through the distal end of the cartridge and is contained or channeled through the odor scrubbing filter media wherein odiferous compounds are preferentially neutralized or scrubbed from the gas and released extracorporeal from the host device. Such compartment or flange containing the odor scrubbing element or filter can be attached to a cap or closure device that at first to host device and assists in fixing the cartridge assembly to the host device. The cap or closure device has vents to allow the escape of gas that has odor elements neutralized or removed. A closure device or cap utilized to independently close the host device and provide containment of the odor-scrubbing element while providing a gas tight seal. Odorous gas is passed through the filter/odor scrubbing or neutralizing element and travels either axially or radially to exit through odor scrubbing media to vents in a closure or cap device.

While it is intended that any of the cartridge embodiments described herein be provided to the user in a non-sterile condition for one use and then discard, it is conceived that such cartridges could be sterilized and supplied to the user in that fashion for single use, or alternately made of re-sterilizable materials for repeated cleansing, sterilization and reuse, if necessary.

In view of the foregoing, it will be seen that the several objects of the invention are achieved and other advantages are attained. Although the foregoing includes a description of the best mode contemplated for carrying out the invention, various modifications are conceivable.

As various modifications could be made in the constructions herein described and illustrated without departing from the scope of the invention it is intended that all matter contained in the foregoing description or shown in the accompanying drawings shall be interpreted as illustrative rather than limiting.

What is claimed is:

1. An ostomy cartridge for use with a host device associated with a mammal, said cartridge including:

a generally cylindrical a body formed at least partially of polymeric material; and a stem secured to the body and operable to permit insertion of the body into the host device, which is dispose within the user's body during use, and removal of the body from the host device, said stem and said body cooperating with one another and associated with the host device to prevent flow of liquid and solid waste through the host device to the exterior of the mammal with which the host device is associated, wherein at least a portion of the body is adapted to absorb and retain liquid waste therein.

2. An ostomy cartridge as set forth in claim 1, wherein said stem and said body are adapted to provide at least one gas flow passage allowing gas to flow through the host device.

3. An ostomy cartridge as set forth in claim 1, including odor scrubber material carried by the body and operable to extract odor from the gas passing through the host device.

4. An ostomy cartridge as set forth in claim 1, and further comprising a fecal guard operatively mounted to a patient proximal end of the stem for disposition internally of the patient's body during use of the cartridge, to selectively prevent flow of fecal material through the host device, to thereby prevent solid materials from entering or fouling gas permeation pathways of the body of the cartridge.

5. An ostomy cartridge as set forth in claim 1, wherein the body includes a fecal guard mounted on the stem and positioned inside of the patient proximal end of the body.

6. An ostomy cartridge as set forth in claim 5, and further comprising a tip mounted on the proximal end of the stem, the tip being adjacent the proximal side of the fecal guard, and having at least one gas flow first opening formed therethrough from a distal side to a proximal side of the tip.

7. An ostomy cartridge as set forth in claim 6, wherein the at least one gas flow first opening includes a slot.

8. An ostomy cartridge as set forth in claim 6, wherein the at least one first opening includes a through hole.

9. An ostomy cartridge as set forth in claim 5, wherein the stem includes an outward projecting ring and said fecal guard includes an internal groove adapted to receive the ring therein for mounting the fecal guard on the stem.

10. An ostomy cartridge as set forth in claim 5, wherein the tip includes a dome-shaped patient proximal end.

11. An ostomy cartridge as set forth in claim 1, including a hydrophobic membrane wrapped around at least a portion of the body.

12. ostomy cartridge as set forth in claim 1, wherein an exterior surface of the body is shaped to form gaps between the body and the host device to allow for movement of the host device.

13. An ostomy cartridge as set forth in claim 12, wherein the exterior surface of the body includes a plurality of spaced-apart ribs that provide support for the host device.

14. An ostomy cartridge as set forth in claim 12, wherein the exterior surface of the body includes at least one portion of a sphere.

15. An ostomy cartridge as set forth in claim 12, wherein the exterior surface of the body includes a plurality of pleats.

16. An ostomy cartridge as set forth in claim 1, wherein an exterior portion of the body if generally cylindrical.

17. An ostomy cartridge as set forth in claim 1, wherein the stem has longitudinally extending elongate channels forming gas flow channels.

18. An ostomy cartridge as set forth in claim 1, wherein the body includes a portion comprising polymeric foam.

19. An ostomy cartridge as set forth in claim 18, wherein at least a portion of the polymeric foam is open cell foam.

20. An ostomy cartridge as set forth in claim 18, wherein at least a portion of the polymeric foam is closed cell foam.

21. An ostomy cartridge as set forth in claim 18, wherein the foam material includes hydrophilic foam.

22. An ostomy cartridge as set forth in claim 21, wherein the body has a proximal end impermeable to solid waste transfer therethrough.

23. An ostomy cartridge for use with a host device associated with a mammal, said cartridge including:

a generally cylindrical body formed at least partially of polymeric material; and a stem secured to the body and operable to permit insertion of the body into the host device, which is disposed within the user's body during use, and removal of the body from the host device, said stem and said body cooperating with one another and associated with thye host device to prevent flow of liquid and solid waste through the host device to the exterior of the mammal with which the host device is associated wherein the stem includes protruding members (12c, 12d) to provide support for the host device.

24. An ostomy cartridge as set forth in claim 23, wherein the body includes a portion comprising polymeric team.

25. An ostomy cartridge as set forth in claim 24, wherein at least a portion of the polymeric foam is open cell form.

26. An ostomy cartridge as set forth in claim 24, wherein at least a portion of the polymeric foam is closed cell foam.

27. An ostomy cartridge as set forth in claim 24, wherein the foam material includes hydrophilic foam.

28. An ostomy cartridge as set forth in claim 27, wherein the body has a proximal end impermeable to solid waste transfer therethrough.

29. An ostomy cartridge as set forth in claim 23, wherein said stem and said body are adapted to provide at least one gas flow passage allowing gas to flow through the host device.

30. An ostomy cartridge as set forth in claim 23, and further comprising a fecal guard operatively mounted to a patient proximal end of the stem for disposition internally of the patient's body during use of the cartridge, to selectively prevent flow of fecal material through the host device, to thereby prevent solid materials from entering or fouling gas permeation pathways of the body of the cartridge.

31. An ostomy cartridge as set forth in claim 23, wherein the body includes a fecal guard mounted on the stem and positioned inside of the patient proximal end of the body.

32. An ostomy cartridge as set forth in claim 31, and further comprising a tip mounted on the proximal end of the stem, the tip bein adjacent the proximal side of the fecal guard, and having at least one gas flow first opening formed therethrough from a distal side to a proximal side of the tip.

33. An ostomy cartridge as set forth in claim 32, wherein the at least one gas flow first opening includes a slot.

34. An ostomy cartridge as set forth in claim 32, wherein the at least one first opening includes a through hole.

35. An ostomy cartridge as set forth in claim 32, wherein the stem includes an outwardly projecting ring an said fecal guard includes an internal groove adapted to receive the ring therein for mounting the fecal guard on the stem.

36. An ostomy cartridge as set forth in claim 31, wherein the tip includes a dome-shaped patient proximal end.

37. An ostomy cartridge as set forth in claim 23, including a hydrophobic membrane wrapped around at least a portion of the body.

38. An ostomy cartridge as set forth in claim 23, wherein an exterior surface of the body is shaped to form gaps between the body and the host device to allow for movement of the host device.

39. An ostomy cartridge as set forth in claim 38, wherein the exterior surface of the body includes a plurality of spaced-apart ribs that provide support for the host device.

40. An ostomy cartridge as set forth in claim 38, wherein the exterior surface of the body includes at least one portion of a sphere.

41. An ostomy cartride as set forth in claim 38, wherein the exterior surface of the body includes a plurality of pleats.

42. An ostomy cartridge as set forth in claim 23, wherein an exterior portion of the body is generaly cylindrical.

43. An ostomy cartridge as set forth in claim 23, wherein the stem has longitudinally extending elongate channels forming gas flow channels.

44. An ostomy cartridge as set forth in claim 23, including odor scrubber material carried by the host and operable to extract odor from the gas passing through the host device.

45. The combination of a host device associated with a mammal and an ostomy cartridge, wherein the ostomy cartridge comprises an elongated cartridge body formed at least partially of polymeric material; and a stem secured to the elongated cartridge body and operable to permit insertion of the elongated cartridge body into the host device, which is disposed within the mammal's body during use, and removal of the elongated cartridge body from the host device, said stem and said elongated cartrige body cooperating with one another and associated with the host device to prevent flow of liquid and solid waste through the host device to the exterior of the mammal with which the host device is associated, wherein the at least a portion of the body is adapted to absorb and retain liquid waste therein; and further wherein the host device comprises a continent ostomy port having a face plate defining a selectively sealable which is alignable wit the opening of a stoma formed in the body of the mammal when the face plate is disposed over the site of the stoma, to thereby provide access to the inside of the stoma; a catheter having a first end and a second end, the first end being connected to and extending from one side of the face plate, the catheter portion extending proximally and the second end of the catheter portion being disposed interior of the mammal's body within the ostomy site when the continent ostomy port is in normal use position, the catheter portion having an interior side wall which extends from the aperture in the face plate to the second end of the catheter portion and which size and shaped approximately for snug, slideable insertion of the cartridge therein.

* * * * *

UNITED STATES PATENT AND TRADEMARK OFFICE
CERTIFICATE OF CORRECTION

PATENT NO. : 7,083,569 B2  Page 1 of 1
APPLICATION NO. : 10/210261
DATED : August 1, 2006
INVENTOR(S) : Jason Boulanger et al.

It is certified that error appears in the above-identified patent and that said Letters Patent is hereby corrected as shown below:

|  | Reads | Should Read |
|---|---|---|
| Col. 9, Line 47 | "12. ostomy" | -- 12. An ostomy -- |
| Col. 9, Line 60 | "body if" | -- body is -- |
| Col. 10, Line 16 | "associated with thye" | -- associated with the -- |
| Col. 10, Line 22 | "polymeric team" | -- polymeric foam. -- |
| Col. 10, Line 56 | "ring an said" | -- ring and said -- |
| Col. 12, Line 9 | "alignable wit the" | -- alignable with the -- |

Signed and Sealed this

Twenty-eighth Day of November, 2006

JON W. DUDAS
*Director of the United States Patent and Trademark Office*